(12) United States Patent
Lee et al.

(10) Patent No.: US 8,822,112 B2
(45) Date of Patent: Sep. 2, 2014

(54) SILOXANE-BASED COMPOUND, PHOTOSENSITIVE COMPOSITION COMPRISING THE SAME AND PHOTOSENSITIVE MATERIAL

(71) Applicant: LG Chem, Ltd., Seoul (KR)

(72) Inventors: Keon Woo Lee, Daejeon (KR); Sang Kyu Kwak, Daejeon (KR); Changsoon Lee, Daejeon (KR); Hyehyeon Kim, Seoul (KR); Saehee Kim, Seoul (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 14/005,151

(22) PCT Filed: Jan. 25, 2013

(86) PCT No.: PCT/KR2013/000600
§ 371 (c)(1),
(2), (4) Date: Sep. 13, 2013

(87) PCT Pub. No.: WO2013/147411
PCT Pub. Date: Mar. 10, 2013

(65) Prior Publication Data
US 2014/0080043 A1    Mar. 20, 2014

(30) Foreign Application Priority Data

Mar. 30, 2012 (KR) .......... 10-2012-0032949
Jan. 24, 2013 (KR) .......... 10-2013-0007949

(51) Int. Cl.
*G03F 7/004* (2006.01)
*C07F 7/10* (2006.01)

(52) U.S. Cl.
USPC .......... 430/18; 430/288.1; 556/423

(58) Field of Classification Search
None
See application file for complete search history.

(56) References Cited

U.S. PATENT DOCUMENTS

| | | | |
|---|---|---|---|
| 5,464,900 A * | 11/1995 | Stofko et al. | 524/838 |
| 6,867,318 B1 | 3/2005 | Cui | |
| 7,813,615 B2 | 10/2010 | Bae et al. | |
| 2004/0077751 A1 | 4/2004 | Kumagat et al. | |
| 2009/0123867 A1 * | 5/2009 | Yuba et al. | 430/270.1 |
| 2009/0162782 A1 | 6/2009 | Takei et al. | |
| 2011/0212006 A1 * | 9/2011 | La et al. | 423/127 |
| 2011/0254133 A1 | 10/2011 | Pohlers | |
| 2011/0293897 A1 | 12/2011 | Kawashima | |

FOREIGN PATENT DOCUMENTS

| | | |
|---|---|---|
| CN | 1976939 A | 6/2007 |
| CN | 102285201 A | 12/2011 |
| EP | 1452536 A1 | 9/2004 |

OTHER PUBLICATIONS

Office Action No. (103) dated Apr. 3, 2014, in corresponding Taiwanese Patent Application No. 102103080, including English translation, 10 pages.

\* cited by examiner

*Primary Examiner* — John A. McPherson
(74) *Attorney, Agent, or Firm* — Rothwell, Figg, Ernst & Manbeck, P.C.

(57) ABSTRACT

The present application relates to a siloxane-based compound, a photosensitive composition including the same, and a photosensitive material.

27 Claims, No Drawings

SILOXANE-BASED COMPOUND, PHOTOSENSITIVE COMPOSITION COMPRISING THE SAME AND PHOTOSENSITIVE MATERIAL

TECHNICAL FIELD

The present application is a 35 U.S.C. §371 National Phase Entry Application from PCT/KR2013/000600, filed Jan. 25, 2013, and designating the U.S., which claims priority to and the benefit of Korean Patent Application No. 10-2012-0032949, filed in the Korean Intellectual Property Office on Mar. 30, 2012, and Korean Patent Application No. 10-2013-0007949, filed in the Korean Intellectual Property Office on Jan. 24, 2013, the entire contents of which are incorporated herein by reference.

The present application relates to a siloxane-based compound, a photosensitive composition including the same, and a photosensitive material.

BACKGROUND ART

Various photoresists are used in the manufacture of a liquid crystal display device. For example, when a color filter is manufactured, a photoresist in which a pigment for forming color pixels is dispersed may be used.

When a black matrix serving as a light blocking layer that blocks light is formed, it is possible to use a solution in which a black pigment, carbon black, perylene black, titanium dioxide and the like are dispersed.

A transparent photoresist in which a pigment is not included may be used in the manufacture of an overcoat that corrects a step height between pixels and a column spacer that maintains the cell-gap of a liquid crystal display device.

A photosensitive composition that is used in a column spacer or an overcoat may also be used for passivation of a thin film transistor layer.

When each photoresist is processed on a glass substrate or a glass substrate coated with indium tin oxide through an appropriate photolithography process according to the specific order, it is possible to form a single color filter plate composed of a multi-layered organic thin film having a thickness of 5 μm or less.

The resolution of a liquid crystal display device may be improved in order to implement a high-level image quality, and for this purpose, the resolution of the color filter may be increased.

DISCLOSURE

Technical Problem

The size of a color pixel, a black matrix, a column spacer, and the like may be decreased in manufacturing a color filter having high resolution, and in this case, adhesion between a photoresist thin film and a lower substrate becomes insufficient during a pattern development process, and thus a defect in which a portion of a pattern is lost may be generated.

In order to solve the problem, there is a need for developing a photosensitive composition with low possibility of losing a thin film during a development process.

Technical Solution

An exemplary embodiment of the present application provides a compound represented by the following Formula 1.

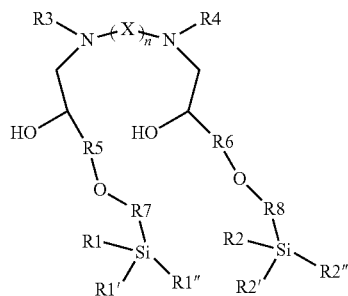

In Formula 1,

R1, R1', R1", R2, R2' and R2" are the same as or different from each other, and each independently an alkoxy group having 1 to 6 carbon atoms, R3 and R4 are the same as or different from each other, and each independently an alkyl group having 1 to 6 carbon atoms, R5, R6, R7 and R8 are the same as or different from each other, and each independently an alkylene group having 1 to 6 carbon atoms, X represents —CRR', and R and R' are the same as or different from each other and each independently hydrogen or an alkyl group having 1 to 6 carbon atoms, and n is an integer from 1 to 10.

Another exemplary embodiment of the present application provides a photosensitive composition comprising: a) the compound represented by Formula 1, b) a crosslinkable compound comprising two or more ethylenically unsaturated bonds, c) an alkali soluble binder resin, d) a photopolymerization initiator, and e) a solvent.

Another exemplary embodiment of the present application provides a pattern formed by using the photosensitive composition.

Another exemplary embodiment of the present application provides a photosensitive material prepared by using the photosensitive composition.

Advantageous Effects

The compound according to an exemplary embodiment of the present application includes siloxane, and may be included in a photosensitive composition. When the photosensitive composition comprising the compound according to an exemplary embodiment of the present application is used, the possibility of losing a thin film during a pattern development process may be reduced, and a thin film with adhesion of a pattern improved may be formed.

MODE FOR INVENTION

Hereinafter, the present application will be described in more detail.

An exemplary embodiment of the present application provides a compound represented by Formula 1.

Formula 1 in an exemplary embodiment of the present application may be represented by the following Formula 2.

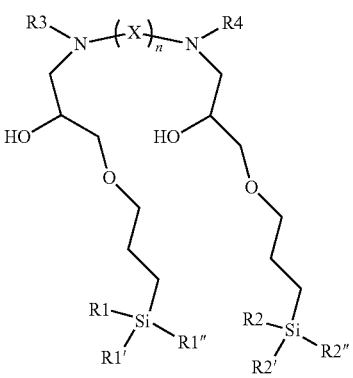

[Formula 2]

In the compound according to an exemplary embodiment of this application, the substituents of Formula 1 or 2 will be described in more detail as follows.

The alkyl group may be a straight or branched chain. Specific examples thereof include a methyl group, an ethyl group, a propyl group, an isopropyl group, a butyl group, a t-butyl group, a pentyl group, a hexyl group or the like, but are not limited thereto.

The alkylene group is a case in which the alkyl group is used as a divalent substituent.

The alkoxy group refers to an oxygen radical substituted with an alkyl group. As an alkyl group, the alkyl group may be used, and an alkoxy group may be a straight or branched chain. Specific examples thereof include methoxy, ethoxy, n-propoxy, n-butoxy, pentoxy or the like, but are not limited thereto.

According to an exemplary embodiment of this application, in Formula 1 or 2, R1, R1', R1", R2, R2' and R2" are the same as or different from each other, and may be each independently a methoxy group or an ethoxy group. According to another exemplary embodiment, in Formula 1 or 2, R3 and R4 are the same as or different from each other, and may be each independently an alkyl group having 1 to 3 carbon atoms.

According to yet another exemplary embodiment, in Formula 1, R5, R6, R7 and R8 are the same as or different from each other, and each independently an alkylene group having 1 to 6 carbon atoms. Specifically, R5 and R6 are the same as or different from each other, and may be each independently a methylene group or an ethylene group. Specifically, R7 and R8 may be a propylene group.

According to still another exemplary embodiment, in Formula 1 or 2, R and R' are hydrogen.

According to still yet another exemplary embodiment, in Formula 1 or 2, n may be an integer from 1 to 3, and is preferably 2 or 3.

An exemplary embodiment of the present application provides a photosensitive composition including: a) the compound represented by Formula 1, b) a crosslinkable compound including two or more unsaturated acrylic bonds, c) an alkali soluble binder resin, d) a photopolymerization initiator, and e) a solvent.

Only one kind of a) the compound represented by Formula 1 may be included in the photosensitive composition, but two or more kinds thereof may also be mixed and included in the photosensitive composition.

In the photosensitive composition according to an exemplary embodiment of this application, a) the compound represented by Formula 1 may be included in an amount from 0.05 wt % to 5 wt % based on the total weight of the total solid except for e) the solvent. An advantageous effect may be obtained when the amount is 0.05 wt % or more, and the storage stability of a product is not inhibited when the compound is included in an amount of 5 wt % or less.

In the photosensitive composition according to an exemplary embodiment of this application, examples of b) the crosslinkable compound including two or more unsaturated acrylic bonds include one or more selected from the group consisting of compounds obtained by esterifying a polyhydric alcohol, such as ethylene glycol di(meth)acrylate, polyethylene glycol di(meth)acrylate having 2 to 14 ethylene groups, trimethylolpropane di(meth)acrylate, trimethylolpropane tri(meth)acrylate, pentaerythritol tri(meth)acrylate, pentaerythritol tetra(meth)acrylate, 2-trisacryloyloxymethylethylphthalic acid, propylene glycol di(meth)acrylate having 2 to 14 propylene groups, dipentaerythritol penta(meth)acrylate, dipentaerythritol hexa(meth)acrylate, a mixture of an acid modified product of dipentaerythritol penta(meth)acrylate and dipentaerythritol hexa(meth)acrylate (trade name:TO-2348 and TO-2349 manufactured by Japanese Toagosei Co., Ltd.) and the like, with α,β-unsaturated carboxylic acids; compounds obtained by adding (meth)acrylic acids to a glycidyl group-containing compound such as a trimethylolpropane triglycidyletheracrylic acid adduct, a bisphenol A diglycidyletheracrylic acid adduct and the like; ester compounds obtained from a polyhydric carboxylic acid and a compound having a hydroxyl group or an ethylenically unsaturated bond, or polyisocyanate adducts of compounds having a hydroxyl group or an ethylenically unsaturated bond, such as phthalic acid diester of β-hydroxyethyl(meth)acrylate, a toluene diisocyannate adduct of β-hydroxyethyl(meth)acrylate, and the like, or adducts with polyisocyanate; (meth)acrylic acid alkyl esters such as methyl (meth)acrylate, ethyl (meth)acrylate, butyl(meth)acrylate, 2-ethylhexyl (meth)acrylate and the like; and 9,9'-bis[4-(2-acryloyloxyethoxy)phenyl]fluorene, and those known in the art may be used without being limited thereto.

In some cases, a silica dispersion may be used in addition to the above-described crosslinkable compound. Examples of the silica dispersion include Nanocryl XP series (0596, 1045 and 21/1364) and Nanopox XP series (0516 and 0525), manufactured by Eanse Chemie Co., Ltd., and the like.

It is preferred that b) the crosslinkable compound including two or more unsaturated acrylic bonds is included in an amount from 1 part by weight to 30 parts by weight based on 100 parts by weight of the entire composition. When the content of the crosslinkable compound is 1 part by weight or more, a crosslinking reaction by light may be advantageously performed. When the content of the crosslinkable compound is 30 parts by weight or less, the solubility with respect to the alkali is not inhibited, which is advantageous in forming a pattern.

In the photosensitive composition according to an exemplary embodiment of this application, an acrylic binder resin containing a carboxylic group may be used as c) the alkali soluble binder resin, and a binder resin having a weight average molecular weight from 3,000 to 150,000 may be used. When the weight average molecular weight of the alkali soluble binder resin is 3,000 or more, heat resistance and chemical resistance are maintained, and when the weight average molecular weight thereof is 150,000 or less, development may be performed while the resin has solubility with respect to a developing solution, which is equal to or more than a predetermined value, and it is possible to uniformly apply the resulting solution because the viscosity of the solution may be maintained.

An alkali soluble binder resin having an acid value from 30 KOH mg/g to 300 KOH mg/g may be used as the alkali soluble binder resin. When the acid value is 30 KOH mg/g or more, development is performed well to obtain clean patterns, and when the acid value is 300 KOH mg/g or less, a washing characteristic is excessively improved to prevent patterns from being fallen off.

It is preferred that c) the alkali soluble binder resin is included in an amount from 1 part by weight to 20 parts by weight based on 100 parts by weight of the entire composition. When the content of the alkali soluble resin is 1 part by weight or more, solubility with respect to the developing solution appears, and thus it is proper to form a pattern, and when the content thereof is 20 parts by weight or less, the viscosity of the entire solution is in a predetermined level or less, which is advantageous in coating the composition.

In the photosensitive composition according to an exemplary embodiment of this application, d) the photopolymerization initiator is not particularly limited, but it is possible to use one or more selected from the group consisting of triazine-based compounds; biimidazole compounds; acetophenone-based compounds; O-acyloxime-based compounds; benzophenone-based compounds; tioxanthone-based compounds; phosphine oxide-based compound; and coumarin-based compounds.

As the non-limiting examples of the photopolymerization initiator, it is possible to use either a triazine-based compound, such as 2,4-trichloromethyl-(4'-methoxyphenyl)-6-triazine, 2,4-trichloromethyl-(4'-methoxystyryl)-6-triazine, 2,4-trichloromethyl-(fipronil)-6-triazine, 2,4-trichloromethyl-(3',4'-dimethoxyphenyl)-6-triazine, 3-{4-[2,4-bis(trichloromethyl)-s-triazine-6-yl]phenylthio}propanoic acid, 2,4-trichloromethyl-(4'-ethylbiphenyl-6-triazine, 2,4-trichloromethyl-(4'-methylbiphenyl)-6-triazine and the like; a biimidazole compound, such as 2,2'-bis(2-chlorophenyl)-4,4',5,5'-tetraphenyl biimidazole, 2,2'-bis(2,3-dichlorophenyl)-4,4',5,5'-tetraphenyl biimidazole and the like; an acetophenone-based compound such as 2-hydroxy-2-methyl-1-phenylpropan-1-one, 1-(4-isopropylphenyl)-2-hydroxy-2-methylpropan-1-one, 4-(2-hydroxyethoxy)-phenyl (2-hydroxy)propyl ketone, 1-hydroxycyclohexyl phenyl ketone, 2,2-dimethoxy-2-phenyl acetophenone, 2-methyl-(4-methylthiophenyl)-2-morpholino-1-propan-1-one (Irgacure-907), 2-benzyl-2-dimethylamino-1-(4-morpholinophenyl)-butan-1-one (Irgacure-369) and the like; an O-acvloxime-based compound, such as Irgacure OXE 01 and Irgacure OXE 02, manufactured by CIBA Geigy Corp.; a benzophenone-based compound, such as 4,4'-bis(dimethylamino)benzophenone 4,4'-bis(diethylamno)benzophenone and the like; a tioxanthone-based compound, such as 2,4-diethyl tioxanthone, 2-chloro tioxanthone, isopropyl tioxanthone, diisopropyl tioxanthone and the like; a phosphine oxide-based compound, such as 2,4,6-trimethylbenzoyl diphenylphosphine oxide, bis(2,6-dimethoxybenzoyl)-2,4,4-trimethylpentyl phosphine oxide, bis(2,6-dichlorobenzoyl) propyl phosphine oxide and the like; a coumarin-based compound, such as 3,3'-carbonylvinyl-7-(diethylamino)coumarin, 3-(2-benzothiazolyl)-7-(diethylamino) coumarin, 3-benzoyl-7-(diethylamino)coumarin, 3-benzoyl-7 methoxy-coumarin, and 10,10'-carbonylbis[1,1,7,7-tetramethyl-2,3,6,7-tetrahydro-1H,3H,11H—Cl]-benzopyrano[6,7,8-ij]-quinolizin-11-one; and the like alone or in a mixture of two or more thereof.

It is preferred that d) the photopolymerization initiator is included in an amount from 0.1 part by weight to 5 parts by weight based on 100 parts by weight of the entire composition. When the content of the photopolymerization initiator is 0.1 part by weight or more, sufficient sensitivity may be obtained, and when the content thereof is 5 parts by weight or less, UV light may be transferred up to the bottom by controlling the UV absorbance.

In the photosensitive composition according to an exemplary embodiment of this application, non-limiting examples of e) the solvent include one or more selected from the group consisting of methyl ethyl ketone, methyl cellosolve, ethyl cellosolve, ethylene glycol dimethyl ether, ethylene glycol diethyl ether, propylene glylcol dimethyl ether, propylene glylcol diethyl ether, diethylene glycol dimethyl ether, diethylene glycol diethyl ether, diethylene glycol methyl ethyl ether, 2-ethoxy propanol, 2-methoxy propanol, 3-methoxy butanol, cyclohexanone, cyclopentanone, propylene glylcol methyl ether acetate, propylene glylcol ethyl ether acetate, 3-methoxybutyl acetate, ethyl 3-ethoxypropionate, ethyl cellosolve acetate, methyl cellosolve acetate, butyl acetate and dipropylene glylcol monomethyl ether, but are not limited thereto.

It is preferred that e) the solvent is included in an amount from 45 parts by weight to 95 parts by weight based on 100 parts by weight of the entire composition.

The photosensitive composition according to an exemplary embodiment of the present application may include a) the compound represented by Formula 1 in an amount from 0.01 part by weight to 1.5 parts by weight, b) the crosslinkable compound including two or more unsaturated acrylic bonds in an amount from 1 part by weight to 30 parts by weight, c) the alkali soluble binder resin in an amount from 1 part by weight to 20 parts by weight, d) the photopolymerization initiator in an amount from 0.1 part by weight to 5 parts by weight, and e) the solvent in an amount from 45 parts by weight to 95 parts by weight, based on 100 parts by weight of the entire composition.

The photosensitive composition according to an exemplary embodiment of the present application may additionally include, if necessary, one or more selected from a colorant, a curing accelerator, a thermal polymerization inhibitor, a plasticizer, an adhesive accelerator, a filler, a photosensitizer or a surfactant, in addition to the constituent components.

As the colorant, one or more pigments, dyes or mixtures thereof may be used. Specific examples of black pigments include metal oxides, such as carbon black, graphite, titan black and the like. Examples of carbon black include SEAST 5HIISAF-HS, SEAST KE, SEAST 3HHAF-HS, SEAST NH, SEAST 3M, SEAST 300HAF-LS, SEAST 116HMMAF-HS, SEAST 116MAF, SEAST FMFEF-HS, SEAST SOFEF, SEAST VGPF, SEAST SVHSRFHS and SEAST SSRF (Tokai Carbon Co., Ltd); DIAGRAM BLACK II, DIAGRAM BLACK N339, DIAGRAM BLACK SH, DIAGRAM BLACK H, DIAGRAM LH, DIAGRAM HA, DIAGRAM SF, DIAGRAM N550M, DIAGRAM M, DIAGRAM E, DIAGRAM G, DIAGRAM R, DIAGRAM N760M, DIAGRAM LR, #2700, #2600, #2400, #2350, #2300, #2200, #1000, #980, #900, MCF88, #52, #50, #47, #45, #45L, #25, #CF9, #95, #3030, #3050, MA7, MA77, MA8, MA11, MA100, MA40, OIL7B, OIL9B, OIL11B, OIL30B and OIL31B (Mitsubishi Chemical Corporation); PRINTEX-U, PRINTEX-V, PRINTEX-140U, PRINTEX-140V, PRINTEX-95, PRINTEX-85, PRINTEX-75, PRINTEX-55, PRINTEX-45, PRINTEX-300, PRINTEX-35, PRINTEX-25, PRINTEX-200, PRINTEX-40, PRINTEX-30, PRINTEX-3, PRINTEX-A, SPECIAL BLACK-550, SPECIAL BLACK-350, SPECIAL BLACK-250, SPECIAL BLACK-100 and LAMP BLACK-101 (Degussa Co., Ltd.); RAVEN-1100ULTRA, RAVEN-1080ULTRA, RAVEN-1060ULTRA, RAVEN-1040, RAVEN-1035, RAVEN-1020, RAVEN-1000, RAVEN-890E, RAVEN-890, RAVEN-880ULTRA, RAVEN-860ULTRA, RAVEN-850, RAVEN-820, RAVEN-790ULTRA, RAVEN-780ULTRA, RAVEN-760ULTRA, RAVEN-520, RAVEN-500, RAVEN-460, RAVEN-450, RAVEN-430ULTRA, RAVEN-420, RAVEN-410, RAVEN-2500ULTRA, RAVEN-2000, RAVEN-1500, RAVEN-1255, RAVEN-1250, RAVEN-1200, RAVEN-1190ULTRA, RAVEN-1170 (Columbia Carbon Co., Ltd.), mixtures thereof, or the like.

Examples of a colored colorant include Carmine 6B (C.I. 12490), Phthalocyanine Green (C.I. 74260), Phthalocyanine Blue (C.I. 74160), Perylene Black (BASF K0084 and K0086), Cyanine Black, Lionol Yellow (C.I. 21090), Lionol Yellow GRO (C.I. 21090), Benzidine Yellow 4T-564D, Victoria Pure Blue (C.I. 42595), C.I. PIGMENT RED 3, 23, 97, 108, 122, 139, 140, 141, 142, 143, 144, 149, 166, 168, 175, 177, 180, 185, 189, 190, 192, 202, 214, 215, 220, 221, 224, 230, 235, 242, 254, 255, 260, 262, 264 and 272; C.I. PIGMENT GREEN 7 and 36; C.I. PIGMENT BLUE 15:1, 15:3, 15:4, 15:6, 16, 22, 28, 36, 60 and 64; C.I. PIGMENT YELLOW 13, 14, 35, 53, 83, 93, 95, 110, 120, 138, 139, 150, 151, 154, 175, 180, 181, 185, 194 and 213; and C.I. PIGMENT VIOLET 15, 19, 23, 29, 32 and 37, and the like, and white and fluorescent pigments and the like may also be used. As a phthalocyanine-based complex compound used as the pigment, it is also possible to use a material that contains zinc as the central metal in addition to copper.

Examples of the curing accelerator include one or more selected from the group consisting of 2-mercaptobenzoimidazole, 2-mercaptobenzothiazole, 2-mercaptobenzooxazole, 2,5-dimercapto-1,3,4-thiadiazole, 2-mercapto-4,6-dimethylaminopyridine, pentaerythritol tetrakis(3-mercaptopropionate), pentaerythritol tris(3-mercaptopropionate), pentaerythritol tetrakis(2-mercaptoacetate), pentaerythritol tris(2-mercaptoacetate), trimethylolpropane tris(2-mercaptoacetate), trimethylolpropane tris(3-mercaptopropionate), trimethylolethane tris(2-mercaptoacetate), and trimethylolethane tris(3-mercaptopropionate), but are not limited thereto and may include those known in the art.

Examples of the thermal polymerization inhibitor include one or more selected from the group consisting of p-anisole, hydroquinone, pyrocatechol, t-butyl catechol, N-nitrosophenylhydroxyamine ammonium salt, N-nitrosophenylhydroxyamine aluminum salt, and phenothiazine, but are not limited thereto and may include those known in the art.

In addition to the constituent components, all the compounds used in the art that may be included in the photosensitive composition may be used as the plasticizers, adhesion promoters, fillers, photosensitizers, surfactants and the like.

When other components are added to the photosensitive composition according to an exemplary embodiment of this application, it is preferred that the colorant and the other additives are included in amounts from 1 part by weight to 20 parts by weight and from 0.01 part by weight to 5 parts by weight, respectively, based on the entire composition.

A pattern may be formed by using the photosensitive composition.

The pattern may be formed by performing exposure and development using a photomask with various aperture diameters, and then drying the pattern.

According to an exemplary embodiment of this application, when a pattern using the photosensitive composition is formed by using a photomask with an aperture width less than 11 μm, the pattern is preserved after development.

This characteristic indicates that the adhesion is excellent even though the pattern is formed in a small size.

The photosensitive composition according to an exemplary embodiment of the present application may be used in a roll coater, a curtain coater, a spin coater, a slot die coater, various printings, dipping and the like, and may be applied on a support such as metal, paper, a glass plastic substrate and the like.

The photosensitive composition may be transferred to other supporters after the composition is applied on a support such as a film and the like, or may be transferred to a blanket and the like and transferred to a second support again after the composition is applied on a first support, and there are no particular limitations on the application methods.

Examples of a light source for curing the photosensitive composition according to an exemplary embodiment of the present application include a mercury vapor arc, a carbon arc, a xenon (Xe) arc and the like, which emit light having a wavelength of 250 nm to 450 nm, but are not limited thereto.

An exemplary embodiment of the present application provides a pattern formed by using the photosensitive composition.

The pattern may be formed by performing exposure and development using a photomask with various aperture diameters, and then drying the pattern.

Even though a photomask part having an aperture width less than 11 μm is used, a shape of the pattern according to an exemplary embodiment of the present application is preserved without being lost at the time of development.

This characteristic indicates that the adhesion is excellent even though the pattern is formed in a small size.

An exemplary embodiment of the present application provides a photosensitive material prepared by using the photosensitive composition.

The photosensitive composition is present in a state in which at least a portion of the solvent is removed or photocured by drying and/or curing the photosensitive material.

The photosensitive material according to an exemplary embodiment of the present application is preferably used in a photoacrylic photosensitive material that serves as a dielectric film when a TFT-LCD or an organic light emitting diode is manufactured, a pigment-dispersion type photosensitive material, a photosensitive material for forming a black matrix, a photosensitive material for forming an overcoat layer or a column spacer photosensitive material, but may also be used in the manufacture of a photocurable paint, a photocurable ink, a photocurable adhesive, a printing plate, a photosensitive material for a printed circuit board, other transparent photosensitizers, PDP, and the like, and there are no particular limitations on the use thereof.

Hereinafter, preferred Examples will be provided for better understanding of this application. However, the following Examples are provided only for the purpose of understanding the present application more easily, but the present application is not limited thereby.

The following Examples illustrate only a portion of the examples according to this application, but it is obvious to those skilled in the art that substantially the same effect as the present application may be obtained even when equivalents thereof are used.

SYNTHETIC EXAMPLE 1

10 mol of N,N'-dimethylethylene diamine (Aldrich) and 20 mol of 3-glycidoxypropyltrimethoxysilane (KBM-403 manufactured by Shin-Etsu Chemical Co., Ltd.) were each diluted in propylene glycol monomethyl ether acetate. While the solution in which N,N'-dimethylethylene diamine was diluted was maintained at 50° C., the solution in which 3-glycidoxypropyltrimethoxysilane (KBM-403 manufactured by Shin-Etsu Chemical Co., Ltd.) was diluted was slowly added thereto to allow the mixture to react. The obtained solution was separated through a column, and then the solvent was removed by using vacuum distillation, thereby obtaining a compound represented by [Formula 3].

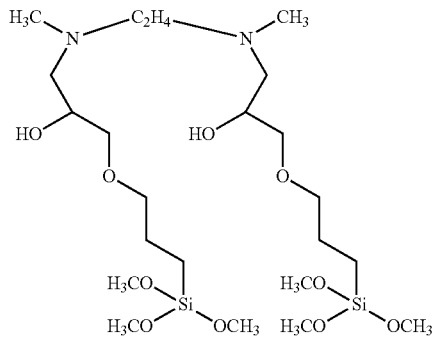

[Formula 3]

The structure was confirmed through $^1$H-NMR. 2.27 (>NCH$_3$), 2.46 (—C$_2$H$_4$—), 2.0 (—OH), 3.55 (—OCH$_3$)

SYNTHETIC EXAMPLE 2

A compound represented by [Formula 4] was obtained by using the same method as in [Synthetic Example 1] to allow the mixture to react, except that 3-glycidoxypropyltriethoxysilane (KBE-403 manufactured by Shin-Etsu Chemical Co., Ltd.) was used instead of 3-glycidoxypropyltrimethoxysilane (KBM-403 manufactured by Shin-Etsu Chemical Co., Ltd.).

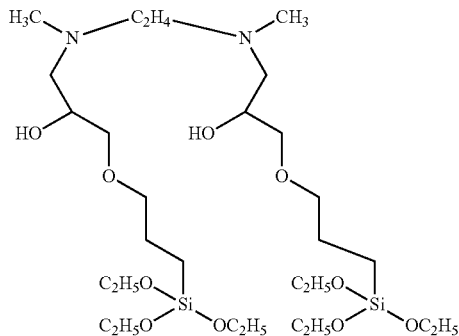

[Formula 4]

The structure was confirmed through $^1$H-NMR. 2.27 (>NCH$_3$), 2.46 (—C$_2$H$_4$—), 2.0 (—OH), 1.22, 3.83 (—OC$_2$H$_5$)

SYNTHETIC EXAMPLE 3

A compound represented by [Formula 5] was obtained by using the same method as in [Synthetic Example 1] to allow the mixture to react, except that N,N'-diethylethylene diamine (Aldrich) was used instead of N,N'-dimethylethylene diamine (Aldrich).

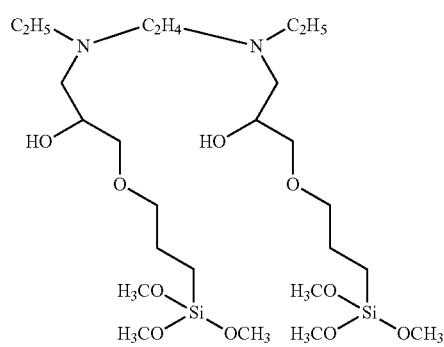

[Formula 5]

The structure was confirmed through $^1$H-NMR. 1.00, 2.40 (>NCH$_2$CH$_3$), 2.46 (—C$_2$H$_4$—), 2.0 (—OH), 3.55 (—OCH$_3$)

SYNTHETIC EXAMPLE 4

A compound represented by [Formula 6] was obtained by using the same method as in [Synthetic Example 3] to allow the mixture to react, except that 3-glycidoxypropyltriethoxysilane (KBE-403 manufactured by Shin-Etsu Chemical Co., Ltd.) was used instead of 3-glycidoxypropyltrimethoxysilane (KBM-403 manufactured by Shin-Etsu Chemical Co., Ltd.).

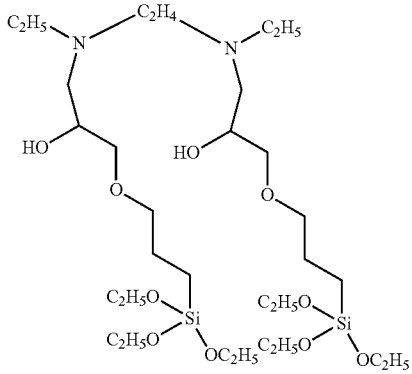

[Formula 6]

The structure was confirmed through $^1$H-NMR. 1.00, 2.40 (>NC$_2$H$_5$), 2.46 (—C$_2$H$_4$—), 2.0 (—OH), 1.22, 3.83 (—OC$_2$H$_5$)

SYNTHETIC EXAMPLE 5

A compound represented by [Formula 7] was obtained by using the same method as in [Synthetic Example 1] to allow the mixture to react, except that N,N'-dimethyl-1,3-propanediamine (Aldrich) was used instead of N,N'-dimethylethylene diamine (Aldrich).

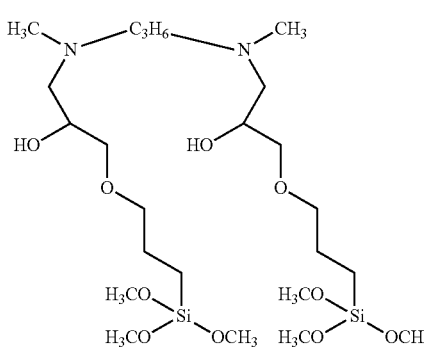

[Formula 7]

The structure was confirmed through $^1$H-NMR. 2.27 (>NCH$_3$), 1.49, 2.36 (—C$_3$H$_6$—), 2.0 (—OH), 3.55 (—OCH$_3$)

SYNTHETIC EXAMPLE 6

A compound represented by [Formula 8] was obtained by using the same method as in [Synthetic Example 5] to allow the mixture to react, except that 3-glycidoxypropyltriethoxysilane (KBE-403 manufactured by Shin-Etsu Chemical Co., Ltd.) was used instead of 3-glycidoxypropyltrimethoxysilane (KBM-403 manufactured by Shin-Etsu Chemical Co., Ltd.).

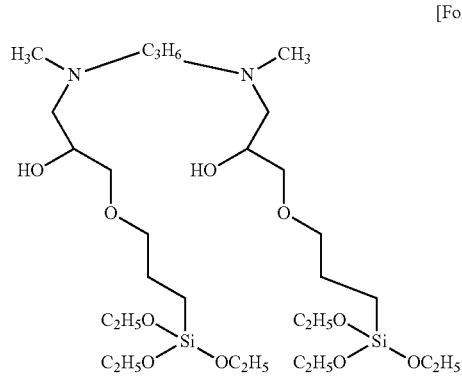

[Formula 8]

The structure was confirmed through $^1$H-NMR. 2.27 (>NCH$_3$), 1.49, 2.36 (—C$_3$H$_6$—), 2.0 (—OH), 1.22, 3.83 (—OC$_2$H$_5$)

SYNTHETIC EXAMPLE 7

A compound represented by [Formula 9] was obtained by using the same method as in [Synthetic Example 1] to allow the mixture to react, except that N,N'-diethyl-1,3-propanediamine (Aldrich) was used instead of N,N'-dimethylethylene diamine (Aldrich).

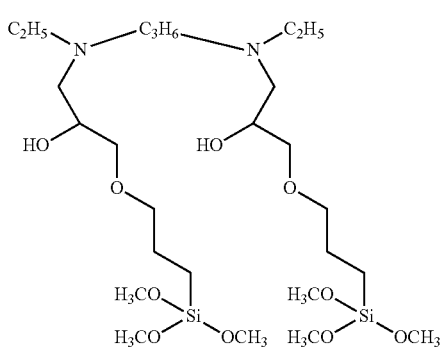

[Formula 9]

The structure was confirmed through $^1$H-NMR. 1.00, 2.40 (>NCH$_2$CH$_3$), 1.49, 2.36 (—C$_3$H$_6$—), 2.0 (—OH), 3.55 (—OCH$_3$)

SYNTHETIC EXAMPLE 8

A compound represented by [Formula 10] was obtained by using the same method as in [Synthetic Example 7] to allow the mixture to react, except that 3-glycidoxypropyltriethoxysilane (KBE-403 manufactured by Shin-Etsu Chemical Co., Ltd.) was used instead of 3-glycidoxypropyltrimethoxysilane (KBM-403 manufactured by Shin-Etsu Chemical Co., Ltd.).

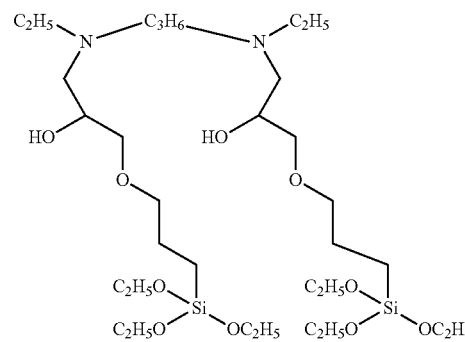

[Formula 10]

The structure was confirmed through $^1$H-NMR. 1.00, 2.40 (>NCH$_2$CH$_3$), 1.49, 2.36 (—C$_3$H$_6$—), 2.0 (—OH), 1.22, 3.83 (—OC$_2$H$_5$)

SYNTHETIC EXAMPLE 9

A compound represented by [Formula 11] was obtained by using the same method as in [Synthetic Example 1] to allow the mixture to react, except that N,N'-diisopropyl-1,3-propanediamine (Aldrich) was used instead of N,N'-dimethylethylene diamine (Aldrich).

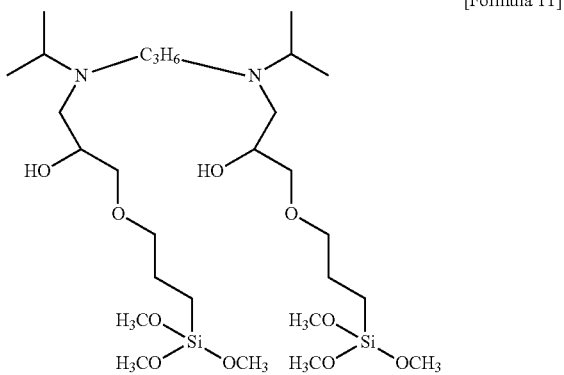

[Formula 11]

The structure was confirmed through $^1$H-NMR. 1.05 (—CH$_3$), 2.97 (>CHN—), 1.49, 2.36 (—C$_3$H$_6$—), 2.0 (—OH), 3.55 (—OCH$_3$)

SYNTHETIC EXAMPLE 10

A compound represented by [Formula 12] was obtained by using the same method as in [Synthetic Example 9] to allow the mixture to react, except that 3-glycidoxypropyltriethoxysilane (KBE-403 manufactured by Shin-Etsu Chemical Co., Ltd.) was used instead of 3-glycidoxypropyltrimethoxysilane (KBM-403 manufactured by Shin-Etsu Chemical Co., Ltd.).

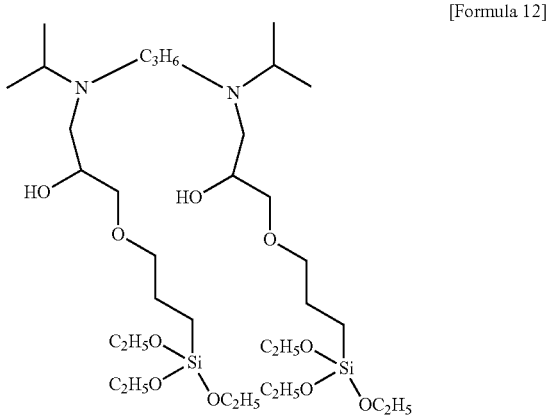

[Formula 12]

The structure was confirmed through $^1$H-NMR. 1.05 (—CH$_3$), 2.97 (>CHN—), 1.49, 2.36 (—C$_3$H$_6$—), 2.0 (—OH), 1.22, 3.83 (—OC$_2$H$_5$)

EXAMPLE 1

In order to confirm the effect of this application, the following photosensitive composition was prepared. 16 g of the binder BzMA/MAA (molar ratio: 70/30, Mw: 24,000) composed of an alkali soluble resin, 8 g of a compound of dipentaerythritol hexaacrylate as a crosslinkable compound, 1 g of Irgacure 369 (2-benzyl-2-dimethylamino-1-(4-morpholinophenyl)-butan-1-one) manufactured by CIBA Geigy Corp. as a photopolymerization initiator, 0.013 g (0.05 wt % based on the total weight of the solid) of the compound of [Formula 3] prepared in [Synthetic Example 1], and PGMEA as an organic solvent were put together such that the content of the entire composition became 100 g, and then a solution, which had been mixed for 3 hours by using a shaker, was obtained with a 5-μm filter and used.

The photosensitive composition was applied using a spin coating method to form a uniform thin film, and then the solvent was volatilized by performing a prebake process at 100° C. for 200 seconds. The thickness of the dried thin film was about 2.5 μm.

The film was exposed under a high pressure mercury lamp by using an independent pattern-type photomask having an aperture diameter from 5 μm to 20 μm, which is constituted at an interval of 1 μm, developed in a spray mode while maintaining the pattern at 30° C. with a KOH alkali aqueous solution having a pH from 11.3 to 11.7, and then washed with pure water and dried by air blowing.

Remaining patterns were observed with an optical microscope after the film was exposed and developed by using a photomask having various diameters, and the smallest pattern among them was used as a reference and the diameter of the photomask used at the time was defined as the size of the pattern.

The storage stability of the composition was measured as follows.

First, the initial viscosity of the composition was measured, the composition was put into a sealed container, the container was left to stand for 24 hours in an oven maintained at 45° C., and then the viscosity was measured again. A value obtained by dividing the degree that the viscosity had been increased by the viscosity initially measured was expressed as % to make a comparison.

EXAMPLE 2

A process was performed in the same manner as in [Example 1], except that 0.253 g (1 wt % based on the total weight of the solid) of the compound of [Formula 3] prepared in [Synthetic Example 1] in [Example 1] was used instead of 0.013 g (0.05 wt % based on the total weight of the solid) thereof.

EXAMPLE 3

A process was performed in the same manner as in [Example 1], except that 1.316 g (5 wt % based on the total weight of the solid) of the compound of [Formula 3] prepared in [Synthetic Example 1] in [Example 1] was used instead of 0.013 g (0.05 wt % based on the total weight of the solid) thereof.

EXAMPLE 4

A process was performed in the same manner as in [Example 1], except that 2.778 g (10 wt % based on the total weight of the solid) of the compound of [Formula 3] prepared in [Synthetic Example 1] in [Example 1] was used instead of 0.013 g (0.05 wt % based on the total weight of the solid) thereof.

EXAMPLES 5 TO 8

A process was performed in the same manner as in [Examples 1 to 4], except that the compound of [Formula 4] prepared in [Synthetic Example 2] was used instead of the compound of [Formula 3] each prepared in [Synthetic Example 1] in [Examples 1 to 4].

EXAMPLES 9 to 12

A process was performed in the same manner as in [Examples 1 to 4], except that the compound of [Formula 5]

prepared in [Synthetic Example 3] was used instead of the compound of [Formula 3] each prepared in [Synthetic Example 1] in [Examples 1 to 4].

EXAMPLES 13 to 16

A process was performed in the same manner as in [Examples 1 to 4], except that the compound of [Formula 6] prepared in [Synthetic Example 4] was used instead of the compound of [Formula 3] each prepared in [Synthetic Example 1] in [Examples 1 to 4].

EXAMPLES 17 to 20

A process was performed in the same manner as in [Examples 1 to 4], except that the compound of [Formula 7] prepared in [Synthetic Example 5] was used instead of the compound of [Formula 3] each prepared in [Synthetic Example 1] in [Examples 1 to 4].

EXAMPLES 21 to 24

A process was performed in the same manner as in [Examples 1 to 4], except that the compound of [Formula 8] prepared in [Synthetic Example 6] was used instead of the compound of [Formula 3] each prepared in [Synthetic Example 1] in [Examples 1 to 4].

EXAMPLES 25 to 28

A process was performed in the same manner as in [Examples 1 to 4], except that the compound of [Formula 9] prepared in [Synthetic Example 7] was used instead of the compound of [Formula 3] each prepared in [Synthetic Example 1] in [Examples 1 to 4].

EXAMPLES 29 to 32

A process was performed in the same manner as in [Examples 1 to 4], except that the compound of [Formula 10] prepared in [Synthetic Example 8] was used instead of the compound of [Formula 3] each prepared in [Synthetic Example 1] in [Examples 1 to 4].

EXAMPLES 33 to 36

A process was performed in the same manner as in [Examples 1 to 4], except that the compound of [Formula 11] prepared in [Synthetic Example 9] was used instead of the compound of [Formula 3] each prepared in [Synthetic Example 1] in [Examples 1 to 4].

EXAMPLES 37 to 40

A process was performed in the same manner as in [Examples 1 to 4], except that the compound of [Formula 12] prepared in [Synthetic Example 10] was used instead of the compound of [Formula 3] each prepared in [Synthetic Example 1] in [Examples 1 to 4].

COMPARATIVE EXAMPLES 1 to 4

A process was performed in the same manner as in [Examples 1 to 4], except that 3-glycidoxypropyltrimethoxysilane (KBM-403 manufactured by Shin-Etsu Chemical Co., Ltd.) was used instead of the compound of [Formula 3] each prepared in [Synthetic Example 1] in [Examples 1 to 4].

COMPARATIVE EXAMPLES 5 to 8

A process was performed in the same manner as in [Examples 1 to 4], except that 3-glycidoxypropyltriethoxysilane (KBE-403 manufactured by Shin-Etsu Chemical Co., Ltd.) was used instead of the compound of [Formula 3] each prepared in [Synthetic Example 1] in [Examples 1 to 4].

COMPARATIVE EXAMPLE 9

A process was performed in the same manner as in [Example 1], except that the compound of [Formula 3] prepared in [Synthetic Example 1] in [Example 1] was not used.

The experimental results of the Examples and the Comparative Examples are summarized as in the following Table 1.

TABLE 1

| Sample | Structure Formula | Content Based on solid content (% by weight) | Content used (g) | Experimental Result Minimum size of remaining pattern (Based on mask) | Storage Stability Variation in viscosity (%) |
|---|---|---|---|---|---|
| Example 1 | Formula 3 | 0.05 | 0.013 | 11 | 0.1 |
| Example 2 |  | 1 | 0.253 | 6 | 0.3 |
| Example 3 |  | 5 | 1.316 | 6 | 1.6 |
| Example 4 |  | 10 | 2.778 | 5 | 4.9 |
| Example 5 | Formula 4 | 0.05 | 0.013 | 9 | 0.3 |
| Example 6 |  | 1 | 0.253 | 7 | 0.5 |
| Example 7 |  | 5 | 1.316 | 7 | 2.3 |
| Example 8 |  | 10 | 2.778 | 6 | 7.8 |
| Example 9 | Formula 5 | 0.05 | 0.013 | 10 | 0.3 |
| Example 10 |  | 1 | 0.253 | 7 | 0.7 |
| Example 11 |  | 5 | 1.316 | 7 | 2.5 |
| Example 12 |  | 10 | 2.778 | 6 | 4.7 |
| Example 13 | Formula 6 | 0.05 | 0.013 | 11 | 0.4 |
| Example 14 |  | 1 | 0.253 | 6 | 2.3 |
| Example 15 |  | 5 | 1.316 | 6 | 2.8 |
| Example 16 |  | 10 | 2.778 | 5 | 3.6 |

TABLE 1-continued

| | Structure | Content | | Experimental Result Minimum | Storage |
| | | Based on solid content (% by weight) | Content used (g) | size of remaining pattern (Based on mask) | Stability Variation in viscosity (%) |
| Sample | Formula | | | | |
|---|---|---|---|---|---|
| Example 17 | Formula 7 | 0.05 | 0.013 | 10 | 0.1 |
| Example 18 | | 1 | 0.253 | 6 | 0.5 |
| Example 19 | | 5 | 1.316 | 6 | 1.4 |
| Example 20 | | 10 | 2.778 | 6 | 5.6 |
| Example 21 | Formula 8 | 0.05 | 0.013 | 9 | 0.1 |
| Example 22 | | 1 | 0.253 | 6 | 1.0 |
| Example 23 | | 5 | 1.316 | 6 | 2.8 |
| Example 24 | | 10 | 2.778 | 5 | 5.9 |
| Example 25 | Formula 9 | 0.05 | 0.013 | 11 | 0.2 |
| Example 26 | | 1 | 0.253 | 6 | 1.4 |
| Example 27 | | 5 | 1.316 | 6 | 2.8 |
| Example 28 | | 10 | 2.778 | 7 | 3.0 |
| Example 29 | Formula 10 | 0.05 | 0.013 | 11 | 0.2 |
| Example 30 | | 1 | 0.253 | 6 | 0.9 |
| Example 31 | | 5 | 1.316 | 6 | 2.1 |
| Example 32 | | 10 | 2.778 | 5 | 3.4 |
| Example 33 | Formula 11 | 0.05 | 0.013 | 9 | 0.1 |
| Example 34 | | 1 | 0.253 | 7 | 0.9 |
| Example 35 | | 5 | 1.316 | 5 | 1.8 |
| Example 36 | | 10 | 2.778 | 5 | 4.4 |
| Example 37 | Formula 12 | 0.05 | 0.013 | 10 | 0.2 |
| Example 38 | | 1 | 0.253 | 7 | 0.9 |
| Example 39 | | 5 | 1.316 | 7 | 2.2 |
| Example 40 | | 10 | 2.778 | 5 | 2.7 |
| Comparative Example 1 | 3-glycidoxypropyltrimethoxysilane | 0.05 | 0.013 | No pattern | 0.1 |
| Comparative Example 2 | | 1 | 0.253 | 19 | 1.1 |
| Comparative Example 3 | | 5 | 1.316 | 19 | 1.7 |
| Comparative Example 4 | | 10 | 2.778 | 17 | 2.6 |
| Comparative Example 5 | 3-glycidoxypropyltriethoxysilane | 0.05 | 0.013 | No pattern | 0.2 |
| Comparative Example 6 | | 1 | 0.253 | 18 | 0.9 |
| Comparative Example 7 | | 5 | 1.316 | 18 | 1.6 |
| Comparative Example 8 | | 10 | 2.778 | 17 | 2.2 |
| Comparative Example 9 | Not including | 0 | | No pattern | 0.1 |

In observing Table 1, it can be known that in Examples 1 to 40, in which the compounds of Formulas 3 to 12 obtained in Synthetic Examples 1 to 10 were used, the adhesion of the pattern was improved and thus even a small size pattern remained compared to Comparative Examples 1 to 8 in which 3-glycidoxypropylmethoxysilane or 3-glycidoxypropyltriethoxysilane, which is a compound used in the related art, was used, or Comparative Example 9 in which no compound was included.

However, when the used amount of the compound according to an exemplary embodiment of the present application exceeds 5% by weight based on the solid content, most of the variations in viscosity exceed 3% in some cases and the safety of the product may be affected.

Accordingly, it is preferred that the compound according to an exemplary embodiment of the present application is applied in an amount from 0.05% by weight to 5% by weight based on the total solid content.

The invention claimed is:

1. A compound represented by the following Formula 1:

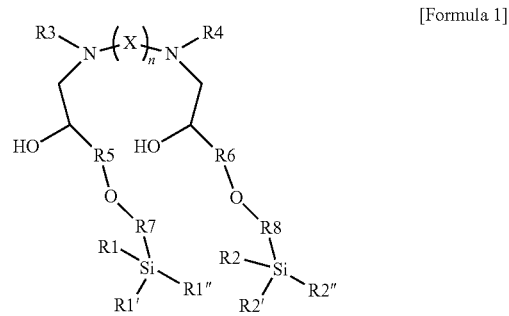

[Formula 1]

in Formula 1,

R1, R1', R1", R2, R2', and R2" are the same as or different from each other, and each independently an alkoxy group having 1 to 6 carbon atoms, R3 and R4 are the same as or different from each other, and each independently an alkyl group having 1 to 6 carbon atoms, R5, R6, R7, and R8 are the same as or different from each other, and each independently an alkylene group having 1 to 6 carbon atoms, X represents -CRR'-, and R and R' are the same as or different from each other and each independently hydrogen or an alkyl group having 1 to 6 carbon atoms, and n is an integer from 1 to 10.

2. The compound according to claim 1, wherein R5, R6, R7, and R8 in Formula 1 are the same as or different from each other, and each independently an alkylene group having 1 to 3 carbon atoms.

3. The compound according to claim 1, wherein R1, R1', R1", R2, R2', and R2" in Formula 1 are the same as or different from each other, and each independently a methoxy group or an ethoxy group.

4. The compound according to claim 1, wherein R3 and R4 in Formula 1 are the same as or different from each other, and each independently an alkyl group having 1 to 3 carbon atoms.

5. The compound according to claim 1, wherein R and R' in Formula 1 are hydrogen.

6. The compound according to claim 1, wherein n in Formula 1 is an integer from 1 to 3.

7. A photosensitive composition comprising:
a) the compound represented by Formula 1 according to claim 1;
b) a crosslinkable compound comprising two or more unsaturated acrylic bonds;
c) an alkali soluble binder resin;
d) a photopolymerization initiator; and
e) a solvent.

8. The photosensitive composition according to claim 7, wherein R5, R6, R7, and R8 in Formula 1 are the same as or different from each other, and each independently an alkylene group having 1 to 3 carbon atoms.

9. The photosensitive composition according to claim 7, wherein R1, R1', R1", R2, R2', and R2" in Formula 1 are the same as or different from each other, and each independently a methoxy group or an ethoxy group.

10. The photosensitive composition according to claim 7, wherein R3 and R4 in Formula 1 are the same as or different from each other, and each independently an alkyl group having 1 to 3 carbon atoms.

11. The photosensitive composition according to claim 7, wherein R and R' in Formula 1 are hydrogen.

12. The photosensitive composition according to claim 7, wherein n in Formula 1 is an integer from 1 to 3.

13. The photosensitive composition according to claim 7, wherein a) the compound represented by Formula 1 is included in an amount from 0.05 wt% to 5 wt% based on the total weight of the solid except for e) the solvent.

14. The photosensitive composition according to claim 7, wherein b) the crosslinkable compound comprising two or more unsaturated acrylic bonds comprises one or two or more selected from the group consisting of compounds obtained by esterifying a polyhydric alcohol with α,β-unsaturated carboxylic acids; compounds obtained by adding (meth)acrylic acids to a glycidyl group-containing compound; ester compounds obtained from a polyhydric carboxylic acid and a compound having a hydroxyl group or an ethylenically unsaturated bond, or polyisocyanate adducts of compounds having a hydroxyl group or an ethylenically unsaturated bond; (meth)acrylic acid alkyl esters; and 9,9'-bis[4-(2-acryloyloxyethoxy)phenyl]fluorene.

15. The photosensitive composition according to claim 7, wherein the photosensitive composition additionally comprises a silica dispersion.

16. The photosensitive composition according to claim 7, wherein c) the alkali soluble binder resin has a weight average molecular weight from 3,000 to 150,000.

17. The photosensitive composition according to claim 7, wherein c) the alkali soluble binder resin has an acid value from 30 KOH mg/g to 300 KOH mg/g.

18. The photosensitive composition according to claim 7, wherein d) the photopolymerization initiator is one or two or more selected from the group consisting of triazine-based compounds; biimidazole compounds; acetophenone-based compounds; O-acyloxime-based compounds; benzophenone-based compounds; tioxanthone-based compounds; phosphine oxide-based compound; and coumarin-based compounds.

19. The photosensitive composition according to claim 7, wherein the photosensitive composition comprises
a) the compound represented by Formula 1 in an amount from 0.01 part by weight to 1.5 parts by weight,
b) the crosslinkable compound comprising two or more unsaturated acrylic bonds in an amount from 1 part by weight to 30 parts by weight,
c) the alkali soluble binder resin in an amount from 1 part by weight to 20 parts by weight,
d) the photopolymerization initiator in an amount from 0.1 part by weight to 5 parts by weight, and
e) the solvent from 45 parts by weight to 95 parts by weight, based on 100 parts by weight of the entire composition.

20. The photosensitive composition according to claim 7, wherein the photosensitive composition additionally comprises one or two or more selected from a colorant, a curing accelerator, a thermal polymerization inhibitor, a plasticizer, an adhesive accelerator, a filler, a photosensitizer, and a surfactant.

21. The photosensitive composition according to claim 20, wherein the colorant is included in an amount from 1 part by weight to 20 parts by weight based on 100 parts by weight of the entire composition.

22. The photosensitive composition according to claim 21, wherein the curing accelerator, the thermal polymerization inhibitor, the plasticizer, the adhesive accelerator, the filler, the photosensitizer or the surfactant is included in an amount from 0.01 part by weight to 5 parts by weight based on 100 parts by weight of the entire composition.

23. The photosensitive composition according to claim 7, wherein when a pattern using the photosensitive composition is formed by using a photomask with an aperture width less than 11 µm, the pattern is preserved after development.

24. A pattern formed by using the photosensitive composition of claim 7.

25. The pattern according to claim 24, wherein when a photomask with an aperture width less than 11 µm is used, a shape of the pattern is preserved at the time of development.

26. A photosensitive material prepared by using the photosensitive composition of claim 7.

27. The photosensitive material according to claim 26, wherein the photosensitive material is a photoacrylic photosensitive material, a pigment-dispersion type photosensitive material, a photosensitive material for forming a black matrix, a photosensitive material for forming an overcoat layer or a column spacer photosensitive material.

* * * * *